United States Patent [19]
McKenzie et al.

[11] Patent Number: 5,491,062
[45] Date of Patent: Feb. 13, 1996

[54] POLYNUCLEOTIDE AMPLIFICATION MYCOPLASMA ASSAY, PRIMERS, AND KITS THEREFORE

[75] Inventors: Douglas T. McKenzie, San Diego; Joseph A. Sorge, Rancho Santa Fe, both of Calif.

[73] Assignee: Stratagene, La Jolla, Calif.

[21] Appl. No.: 158,681

[22] Filed: Nov. 23, 1993

[51] Int. Cl.[6] .............................. C12Q 1/68; C07H 21/04; C12P 19/34
[52] U.S. Cl. ........................... 435/6; 435/912; 536/24.32; 536/24.33; 935/17; 935/78
[58] Field of Search ................... 435/6, 91.2; 536/24.32, 536/24.33; 935/77, 78

[56] References Cited

FOREIGN PATENT DOCUMENTS 9214844  9/1992  WIPO .

OTHER PUBLICATIONS

Van Kuppeveld, Applied and Environmental Biology (1992, Aug.) 58:2606–2615.

*Primary Examiner*—W. Gary Jones
*Assistant Examiner*—Carla Myers
*Attorney, Agent, or Firm*—Albert P. Halluin; Pennie & Edmonds

[57] ABSTRACT

The invention described herein consists of methods and materials for the detection of mycoplasma infections. Mycoplasma infections may be detected in cell cultures and in animals. The subject methods use polynucleotide primer pairs that are capable of hybridizing to mycoplasma tRNA genes so as to provide for the generation of a distinctive set of amplification products when the primers are used in a cyclic amplification synthesis reaction, such as PCR (polymerase chain reaction). In addition to detecting mycoplasma infections, the subject methods may be used to identify the particular species of mycoplasma causing the infection. The subject invention also provides for primers and kits for performing the subject methods.

8 Claims, No Drawings

5,491,062

POLYNUCLEOTIDE AMPLIFICATION MYCOPLASMA ASSAY, PRIMERS, AND KITS THEREFORE

TECHNICAL FIELD OF THE INVENTION

The invention relates to the field of microbiological diagnostics. More specifically, the invention relates to methods and compositions for the detection of mycoplasma infections.

BACKGROUND OF THE INVENTION

Mycoplasmas are wall-less eubacteria which exist as parasites within eucaryotic cells. They are the smallest, simplest, and most primitive form of self-replicating procaryotes, consisting of only three major components—a plasma membrane, ribosomes, and a double-stranded genome of 75–150 kB. The limited biosynthetic capacity of these organisms accounts for their dependence on host cells as a source of nutrients. Mycoplasma are phylogenetically related to gram-positive bacteria such as Bacillus spp. and Clostridium spp. Their size, 300 to 800 nm in diameter, is similar to that of a large virus. Mycoplasmas can be either coccoid, helical, or filamentous in shape.

Mycoplasma are generally characterized on the basis of their host association. In man, infection with respiratory mycoplasmas can lead to a benign, self-limiting, moderately troublesome disease which may yield pulmonary, gastrointestinal, cardiac, and hematological complications. A different set of mycoplasmas are responsible for infections of the human urogenital tract, and an attendant set of complications. In contrast to those mycoplasmas which infect human cells, there is a distinct group of mycoplasma strains which are associated with the infection of cell lines grown in tissue culture. While these infections pose no health threat to the researcher working with the infected cell, they can have major impact on the normal physiology and structural integrity of the infected cell. Table 1, below, describes the range of effects which mycoplasma can have on cell cultures. Because of the breadth of cellular responses which are influenced by mycoplasma infections, researchers must question the validity of any experimental results obtained with infected cells. This concern over the effects of mycoplasma infections on cell responses has provided the impetus for developing methods for detection of infection in cell cultures. Numerous techniques for the detection of mycoplasma have been described. They have been based on microbiological, biochemical, biophysical, and microscopic detection systems. The strengths and weaknesses of each of these techniques has been comprehensively reviewed, "Gene Probe Detection of Human and Cell Culture Mycoplasmas," by Dular, in *Gene Probes for Bacteria,* Academic Press, San Diego (1990). There are two detection techniques which have been found to be the most reliable indicators of mycoplasma infection. The first of these is the MycoTect™ kit marketed by Gibco. This kit is based on the fact that mycoplasma express the gene for adenosine phosphorylase, and as such, will metabolize the suicide substrate 6-methylpurine deoxyriboside into 6-methylpurine and 6-methylriboside, two compounds which are toxic for eucaryotic cells. In this test, cell-free culture supernatants taken from test cells are mixed with the suicide substrate, and then added to cultures of the non-infected indicator cell line 3T6. After several days, the indicator cells are inspected for viability, and cell death is used as a indicator of mycoplasma infection in the test cells.

The other test for mycoplasma which has gained wide acceptance is the rRNA hybridization probe technology of GenProbe™. This test uses a radiolabeled complementary DNA "specific" for mycoplasma to probe for the presence of mycoplasma rRNA. Cell-free culture supernatants taken from test cells are incubated with the radiolabeled probe. The free probe is separated from the bound probe using a hydroxyapatite column; the duplexed probe comes out in the column void volume. The detection of radioactivity in the void above a certain threshold value is indicative of mycoplasma infection. New versions of the GenProbe™ kit (Mycoplasm T.C. II) use a centrifugation and washing step, instead of a column, to separate free radioactivity from bound radioactivity.

Each of the currently accepted tests have drawbacks to their technology. The MycoTect™ detection system requires that the investigator culture his/her test cells in the absence of antibiotics for several passages before culture supernatants can be taken for testing. Because this test is based on the response of an indicator cell line, it is several days (4–5 days) before the results are obtained. Both versions of the GenProbe™ probe test require a separation step which is time-consuming and because the readout utilizes radioactivity, it generates radioactive waste.

Because of the shortcomings of these tests, it is of interest to develop an improved test system for the detection of mycoplasma that avoids these shortcomings. Accordingly, a new sensitive, convenient and efficient test system for the detection and identification of mycoplasma is described herein.

SUMMARY OF THE INVENTION

The present invention involves a method of detecting the presence of mycoplasma in samples for analysis, typically from cell cultures suspected of harboring a mycoplasma infection.

The subject methods involve the use of polynucleotide primers capable of hybridizing to tRNA genes in a mycoplasma genome and the use of a cyclic amplification reaction in a manner so as to produce a mycoplasma specific set of amplification products derived from one or more portions of tRNA genes of one or more tRNA genes, or portions thereof. The amplification product(s) produced by the primers in conjunction with the amplification process, typically polymerase chain reaction (PCR), may be analyzed by electro-

TABLE 1

Effects of Mycoplasmas on Cell Cultures

Interference with the growth rate of cells
Inhibition of lymphocyte transformation
Stimulation of lymphocyte transformation
Induction of morphological alterations, including cytopathology
Altered DNA, RNA, and protein synthesis
Alterations of ribosomal RNA profiles
Alteration of enzyme patterns
Interference with selection of mutant mammalian cells
Induction of chromosomal aberrations
Depletion of the essential amino acid arginine from cell culture growth medium
Inhibition of virus yields
Enhancement of virus yields
Co-purification of mycoplasmas with cell organelles (e.g., mitochondria)
Redistribution and modification of host cell plasma membrane antigens
Apparent reduction in tumorigenic potential of malignant cells phoresis so as to produce an "amplification fingerprint" distinctive for mycoplasma, as well as the particular mycoplasma species causing the infection.

Another aspect of the invention is to provide polynucleotide primers for use in the subject method of detecting the presence of mycoplasma.

The present invention also provides kits for performing the method of detecting/identifying mycoplasma infections. The kits may include one or more of the following items: polynucleotide primers, internal control templates, positive controls, negative controls buffers, enzymes, nucleotides, reagents for isolation of DNA samples and instructions.

DESCRIPTION OF THE SPECIFIC EMBODIMENTS

The present invention relates to a method of detecting mycoplasma infections through the use of intergenic length polymorphism (ILP) PCR technology as described by Welsh and McClelland, *Nucleic Acids Research* 19:861–866 (1991), specifically adapted for use by the inventors for the detection of mycoplasma infections and for the identification of the species of mycoplasma causing the infection. ILP PCR is able to work, in part, due to the organization of tRNA genes within the genome. The organization of tRNA genes varies substantially between organisms. Typically, tRNA genes in procaryotes exist in several clusters of genes scattered throughout the genome. These tRNA gene clusters may contain one or more tRNA genes. Different organisms may contain different tRNA genes in each gene cluster. Additionally, the distance between the tRNA genes (intergenic distances) within a cluster may vary between species and within species. By employing the polymerase chain reaction (variants of PCR and other primer-dependent polynucleotide amplification techniques, e.g., ligase chain reaction (LCR)) to amplify one or more tRNA genes present in a sample for analysis (or portions thereof), a distinctive set of polynucleotide amplification products is produced. The variation in the distances between tRNA genes within a tRNA gene cluster, the identity of tRNA genes within a cluster, and the ability of polynucleotide primers used for the amplification reaction to hybridize to the various tRNA genes present in the different clusters. The distinctive set of polynucleotide amplification products produced by DNA amplification reactions employing tRNA specific hybridization primers is referred to as an "amplification product pattern."

The subject method of detecting mycoplasma infections employs a polynucleotide amplification step. Any of a variety of DNA amplification procedures may be used to carry out the polynucleotide amplification step, provided the amplification employs at least one, and preferably two, polynucleotide primers as initiation sites for the amplification reaction.

A preferred amplification method is the polymerase chain reaction. The technique of the polymerase chain reaction (PCR) is described in detail in various U.S. patents including U.S. Pat. Nos. 4,683,202, 4,683,194, 4,800,195 and 4,965, 188, as well as various publications such as *PCR Protocols: A Guide to Methods and Applications,* by Innis et al., *Academic Press,* San Diego, Calif. (1990), *PCR A Practical Approach,* by McPherson et al., IRL Press at Oxford University (1991), *PCR Technology: Principles and Applications for DNA Amplification,* by Erlich, Stockton Press, New York, N.Y. (1989). While PCR is the preferred means of polynucleotide sequence amplification for use in the subject methods, many variations of PCR exist and may be developed that are functionally the same as PCR in that these techniques involved the use of primer mediated synthesis and repeated cycles of primer annealing, synthesis, and denaturation of double-stranded polynucleotides. The term "cyclic amplification reaction" as used herein refers to PCR and to similar methods of polynucleotide amplification employing primers, and repeated cycles of synthesis, annealing, and denaturation.

Cyclic amplification reactions, e.g., PCR, involve the step of hybridizing, i.e., annealing, a polynucleotide primer to a target polynucleotide. The term "hybridization" refers to the formation of a duplex between two single-stranded polynucleotide molecules. The conditions under which hybridization takes place may be varied so as to permit varying degrees of nucleotide pair mismatch between the duplex pair members. Hybridzation under the most stringent hybridization conditions does not allow duplexes to be formed between between primers and target sequences that contain base pair mismatches. By reducing the stringency of hybridization conditions, duplexes may be formed that contain increasing numbers of base pair mismatches as the stringency is decreased. Methods of adjusting the stringency of nucleic acid hybridizations are well known to the person of average skill in the art, these methods are described, among other places, in Sambrook et al., *Molecular Cloning: A Laboratory Manual,* 2nd Ed., Cold Spring Harbor Laboratory Press, Cold Spring Harbor, N.Y. (1989), and Berger & Kimmel, *Guide to Molecular Cloning Techniques: Methods of Enzymology* Volume 152, Academic Press, San Diego, Calif. (1987).

The amplification step of the subject method of mycoplasma detection/identification produces one or more amplification products. An "amplification product" is a double stranded nucleic acid, usually DNA, that is produced from a polymerase-mediated polynucleotide synthesis reaction primed from a pair of oligonucleotide primers. Depending upon the choice of amplification primer pairs, the amplification step of the subject invention may produce one or more different amplification products.

The primers for use in the amplification step of the subject method for detection of mycoplasma infections are oligonucleotides and may be of any length and sequence so as to provide initiation of polymerization from tRNA genes present in a mycoplasma genome. The term "primer" as used herein refers to a molecule comprised of two or more deoxyribonucleotides or ribonucleotides, preferably more than seven, which are capable of acting as a point of initiation of synthesis when placed under conditions in which synthesis of a primary extension product which is substantially complementary to a nucleic acid strand is induced, i.e., in the presence of nucleoside triphosphates and an agent for polymerization such as DNA polymerase and at a suitable temperature and pH. The primer is preferably single-stranded, however, the primer may be double-stranded, provided separation of the strands takes place prior to hybridization of the primer to a tRNA gene target or tRNA gene cluster intrageneic region, i.e., regions between tRNA genes. The primer must be sufficiently long to prime the synthesis of extension products in the presence of the inducing agent for polymerization. For purposes herein, the oligonucleotide primer typically contains 15–25 or more nucleotides, although it may contain fewer nucleotides. Persons skilled in the art will realize the primers may be readily modified so as to contain additional nucleotide sequences adjacent to the 5' or 3' end of the primers so as to provide for convenient genetic manipulation, detection, or physical manipulation, of the amplification products produced by using the primers in conjunction with a cyclic amplification reaction. The primers of the subject invention are capable of hybridizing to the tRNA genes of mycoplasma organisms. Preferred embodiments of the primers of the subject invention are:

Primer 772 5'CGAAGGGTCGCAGGTTCAAA3'
(SEQ ID No: 1),
Primer 773 5'CAGTCTGCTGCTCTACCGACTGAG3'
(SEQ ID No: 2),
Primer 774, 5'CTCAGTCGGTTAGAGCAGCAG3'
(SEQ ID No: 3),
Primer 964 5'AGGTCGCGGGTTCGAATCC3'
(SEQ ID No: 4),
Primer 965 5'AGTCCGGTGCTCTAACCAACTGAG3'
(SEQ ID No: 5),
Primer 415 5'CGGAGGYCGCAGGTTCGAG3'
(SEQ ID No: 6)

Y may be a T or C. Primers 772 and 773 are particularly preferred.

The subject primers are designed to be used in pairs, wherein each member of the primer pair is capable of hybridizing to different strands of a tRNA gene cluster (or more than one tRNA gene cluster) in an orientation relative to each other capable of supporting the amplification of the polynucleotide region between the annealed primers in a cyclic amplification reaction. Preferred pairs of primers are: (1) Primer 964 and 965, (2) 772 and 773, (3) 772 and 965, (4) 964 and 773, (5) 964 and 774, (6) 415 and 965, (7) 415 and 773, (8) 415 and 774, and (9) 772 and 774. Primer pair 772 and 773 is particularly preferred.

The oligonucleotide primers may be prepared using any convenient method of oligonucleotide synthesis, such as, for example the phosphotriester and phosphodiester methods of in vitro synthesis, or automated embodiments thereof. One such automated embodiment employs diethylphosphoamidites as starting materials and may be synthesized as described by Beaucage et al. *Tetrahedron Letters* 22:1859–1862 (1981). Another suitable method of synthesizing oligonucleotides is to synthesize the oligonucleotides on a modified solid support as described in U.S. Pat. No. 4,458,066.

Samples for analysis by the subject method may be prepared by any of a variety of widely known methods for preparation of polynucleotides in a form suitable for use with cyclic amplification reactions. Polynucleotides may be extracted from tissue samples of a patient (including animals) suspected of harboring a mycoplasma infection, or in a preferred embodiment, from cells isolated from a cell culture suspected of harboring a mycoplasma infection. Methods of isolating polynucleotide samples for amplification from samples for analysis for use in the subject methods of mycoplasma detection/identification are by means of conventional polynucleic acid isolation techniques. These techniques are described, among other places, in Sambrook et al., *Molecular Cloning: A Laboratory Manual*, 2nd Ed., Coldspring Harbor Laboratory Press, Coldspring Harbor, N.Y. (1989), Davies, *Genome Analysis: A Practical Approach*, IRL Press, Oxford, England (1988), Berger & Kimmel, *Guide to Molecular Cloning Techniques: Methods of Enzymology* Volume 152, Academic Press, San Diego, Calif. (1987). The preferred method of isolating polynucleic acid for analysis by the subject methods is by means of a boiling extraction of genomic polynucleic acid from cells as described in Section I.D.2.c of the examples as given below.

The amplification products produced by using the subject primers in the subject assays may be used to determine the presence or absence of a mycoplasma infection, and may also be used to determine the identity of the particular mycoplasma species causing the mycoplasma infection. Mycoplasma cells may be detected and identified on the basis of the sizes of the amplification products produced using the subject methods. Amplification using the subject primers may produce one or more different sized amplification products depending upon which tRNA genes the primer pair is hybridized to at the inception of the amplification reaction. Because of the interspecies (and intraspecies) differences in (1) the chromosomal organization of mycoplasma tRNA genes and (2) the nucleotide sequences of individual mycoplasma tRNA genes, the amplification products produced from mycoplasma tRNA genes using the subject primers in amplification reactions produce a set of amplification products distinctive for mycoplasma. Thus, the subject primers may be used to detect a mycoplasma infection in the presence of non-mycoplasma cells because of the distinctive set of amplification products produced applying the PCR technique to the mycoplasma cell genomes. Additionally, by selecting the proper primers, the amplification products produced can be used to distinguish mycoplasma species from one another. The term "amplification product pattern" refers to the distinctive set of amplification products produced by an amplification reaction using the subject primers. Amplification product patterns for different organisms may differ from one another. The amplification product pattern may be detected by means of any of a variety of commonly available nucleic acid separation techniques, electrophoresis being a particularly preferred separation technique. Thus, the amplification product pattern may be detected by electrophoresis which separates the various amplification products into different size nucleic sequence fragments. Amplification product patterns for different mycoplasma species produced by the cyclic amplification reactions using the subject primers may be produced using polynucleotide samples isolated from previously identified mycoplasma isolates so as to provide amplification product patterns for identification without the need to run positive control samples when analyzing cells suspected of harboring mycoplasma.

The subject methods may comprise the step of including an internal amplification control sequence. The term "internal amplification control sequence" refers to a double-stranded polynucleotide capable of hybridizing to both of the subject oligonucleotide primers under the amplification reaction conditions so as to provide for the amplification of the amplification control sequence. Inclusion of an amplification control sequence in a sample for analysis may be used to verify that the amplification process is indeed taking place and that any failure to see mycoplasma specific amplification product pattern is the result of the absence of mycoplasma as opposed to a failure of the reaction to properly take place.

When performing the subject method for detection of mycoplasmas, negative controls are preferably included. Negative controls may be prepared by producing a polynucleotides extract from cells similar to the cells for analysis, but known to in fact lack a mycoplasma infection. In addition to including negative controls, positive controls may also be performed when performing the subject detection/identification methods on a sample for analysis. Positive controls may be polynucleotides isolated from known mycoplasma or polynucleotides isolated from cells known to be infected with mycoplasma.

The invention herein also contemplates a kit format which comprises a package unit having one or more containers of the subject primers and/or container of reagents used for performing the subject methods of mycoplasma detection. The kit may also contain one or more of the following items: polymerization enzymes, nucleotides for the amplification reaction, instructions, internal amplification controls, data describing amplification product patterns, and reagents for the isolation of genomic DNA in a form suitable for amplification. Kits may contain containers of reagents mixed together in suitable proportions for performing the subject methods. Reagent containers preferably contain reagents in unit quantities that obviate measuring steps when performing the subject methods.

The following examples are offered for the purpose of illustrating, not limiting, the subject invention.

EXAMPLES

I. MATERIALS AND METHODS

A. Mycoplasma: Untitered crude stocks of mycoplasma were obtained from the American Type Culture Collection (ATCC). These stocks were rehydrated with 100 µl of sterilized, HPLC grade water that had been subjected to UV-irradiation (1200 mJ/cm$^3$, Stratalinker™, Stratagene, La Jolla, Calif.). Portions of the freshly re-hydrated mycoplasma stocks were used to infect 3T6 cells (see below), and the remainder was stored at −20° C.

B. Cell Lines: The mycoplasma sensitive cell line, 3T6, was obtained from ATCC, and grown in Dulbecco's Minimal Essential Medium (High Glucose) that had been supplemented with fetal calf serum, sodium pyruvate, penicillin, streptomycin, L-glutamine, non-essential amino acids, and 2-mercaptoethanol. No antibiotics were used in the culture of these cells. The 3T6 cells were passaged every other day, and maintained in a 7.5% $CO_2$ incubator. These cells were used as indicator cells in the Mycotek™ Mycoplasm test (see below) and as targets for intentional infections with mycoplasma stocks (see below).

The cell line ALEX was obtained from the U.C.S.D. (University of California, San Diego) cell culture core facility after having been tested positive for mycoplasma. Another cell line, L cell, was obtained in-house after testing at U.C.S.D. cell culture core facility also showed it to be infected with mycoplasma. The cell lines, SP20 and J558, were tested at U.C.S.D. cell culture core facility and found to be negative for mycoplasma. The U.C.S.D. facility uses the GenProbe™ technique in the analysis of mycoplasma infection in cells.

The 3T6 cell lines were intentionally infected with ATCC stocks of mycoplasma. 3T6 cells were trypsinized off the plate, washed into fresh media, and portions (500 µl) of the cells were incubated with 10–50 µl aliquots of the Mycoplasma stocks for 10 minutes at room temperature. Thereafter, the cells were diluted into 25 mls of media and seeded into a 75 cm$^2$ tissue "vented" tissue culture flasks. This plating procedure resulted in cultures which were immediately 20% confluent. The seeding of each mycoplasma strain was conducted at one hour intervals to minimize the chance for cross-contamination. All cells that had been exposed to mycoplasma, or were known to be infected with mycoplasma, were grown in an isolation incubator separate from non-infected cells. Likewise, infected cells were grown in 75 cm$^2$ "vented" (i.e., possessing a gas-permeable membrane at the top of the flask) tissue cultures flasks to prevent cross-contamination between different cell lines. This filter allows gas exchange to occur even if the top of the flask is tightened completely.

C. Primers: Two sets of primers were used throughout this research. The first set, 964 and 965, are consensus primers designed for use in analyzing intergenic length polymorphisms (ILPs) between tRNA genes, see Welsh and McClelland, *Nucleic Acids Research* 19:861–866 (1991).

The second set of primers are 772 and 773. 772 is a 5' primer which is complementary to a region of both the *M. capricolum* and *M. mycoides* PRO$^{TGG}$ tRNA gene. 733 is a 3' primer which is complementary to a region of both the *M. capricolum* and *M. mycoides* PHE$^{GAA}$ tRNA gene. The tRNA genes for both primers are located in the tRNA genes found in mycoplasmas, see Muto et al., *Nucl. Acids Res.*, 17:5037 (1990), Samuelson, et al., *Biochem. J.*, 232:223–228 (1985) for details of mycoplasma tRNA gene organization.

The 3' primers, 965 and 773, are designed to anneal at equivalent sites with the tRNA genes, whereas the 5' primers, 964 and 772 are offset three b.p. relative to one another with respect to their position of annealing within the tRNA gene. The 772 primer ends in AAA, a nucleotide pattern which is rare in the T1 gene cluster in mycoplasma. Additional information as to the design of primers is presented in Results section B.

The sequence of the primers is as follows:

| |
|---|
| 964 5'AGGTCGCGGGTTCGAATCC3' (SEQ ID No: 4) |
| 772 5'CGAAGGGTCGCAGGTTCAAA3' (SEQ ID No: 1), |
| 965 5'AGTCCGGTGCTCTAACCAACTGAG3' (SEQ ID No: 5), |
| 773 5'CAGTCTGCTGCTCTACCGACTGAG3' (SEQ ID No: 2), |

D. PCR Method: The basic polymerase chain reaction method used was a modification of the method previously described by Welsh and McClelland, *Nucleic Acids Research*, 19:861–866 (1991).

1. The original technique for the analysis of intergenic length polymorphisms (ILPs) between tRNA genes (2) calls for the use of consensus primers under conditions of low-stringency. All water used in making stocks or dilutions thereof, as well as all buffer and water combinations used in making PCR common reactions mixes, were irradiated with UV light (1200 $mJ/cm^2$, Stratalinker™) before use. Likewise, all tips used in pipeting reagents were from high quality commercial sources, and were discarded between each pipetings. Gloves were worn at all times, and frequently changed to prevent carryover between samples.
2. Templates for PCR consisted of several types. There was a) crude ATCC Mycoplasm stocks, b) genomic DNA (gDNA) from cells prepared according to standard methods, and c) crude cell lysates prepared by boiling cells.

a) Preparation of crude ATCC stocks for PCR. Crude mycoplasma stocks (see above) were diluted with UV-irradiated water to appropriate concentrations and added directly to the PCR reaction.

b) Standard extraction of genomic DNA from cells. Cells ($5\times10^5$ to $2\times10^6$) were pelleted, resuspended in 10T1E containing 1% SDS and 200 μg/ml proteinase K, and incubated at 37° C. for 4–16 hours. An equal volume of tris-buffered (pH 7.0) phenol/chloroform (1:1) was added, and the tube was subjected to a 20 minute centrifugation at 12,000×g. The upper aqueous phase was removed to a new tube and subjected to a second extraction with tris-buffered phenolchloroform. The aqueous phase from the second extraction was recovered, made 2M in ammonium acetate and mixed with two and one-half volumes of cold ethanol. The sample was chilled to 4° C. and centrifuged for 20 minutes at 12,000×g. The ethanol was removed, the pellet allowed to dry, and 100 μl of UV-irradiated 10T1E (10 mm Tris HCl pH 7.5 1 mm EDTA) used to rehydrate the pellet. These stocks were diluted with UV-irradiated water to appropriate concentrations and added directly to the PCR reaction. Stock gDNA was stored at 4° C.

c) Boiling extraction of genomic DNA from cells. Cells (>$10^6$) were washed three times with Dulbecco's Phosphate Buffered Saline (PBS) and counted. One million cells were aliquoted into a single eppendorf tube and centrifuged. The cell pellet was resuspended into 100 μl of 1X Taq reaction buffer that had been made with UV-irradiated (1200 mj/$cm^2$, Stratalinker™). The tubes were placed into a boiling water bath for 15 minutes, after which time they were momentarily centrifuged to pellet the cellular debris. The unpelleted crude lysate was diluted with UV-irradiated water to appropriate concentrations, and added directly to the PCR reaction. Residual lysate was not retained. In certain experiments, the crude cell lysate was treated with Strataclean™ (obtained from Stratagene Cloning Systems, Inc.) (10 μl of suspended resin/tube) to remove residual components which interfered with the PCR reaction.

3. PCR reaction conditions.

a) Reaction mixture. PCR reactions were conducted in 50 μl. Common reaction mixtures were made and aliquoted before addition of template. In making the common reaction mixtures, the buffer and water were UV-irradiated (1200 mJ/$cm^2$) before addition of the other components. Complete reaction mixes were overlaid with mineral oil or light silicon oil. The following reaction mixture was made for each reaction.

32.4 μl water

5 μl 10X Taq reaction buffer 0.4 μl dNTPs (stock 25 mM, final concentration 200 μM)

0.2 μl Taq DNA polymerase (stock 5 units/μl) (1 unit/reaction)

2 μl Primers (1 μM final of each primer)

10μl template (concentration dependent on sample, typically 30–100 ng total DNA/reaction).

b) PCR program. The following PCR program is a modification of the program used by Welsh and McCelland, *Nucleic Acids Research* 19:861–866 (1991). It has been modified to maximize the signal-to-noise ratio (see discussion in Results, Section E).

| Program 1 | 92° C. 5 minutes<br>55° C. 1 minute 45 seconds | 1 cycles |
|---|---|---|
| Program 2 | 70° C. 3 minutes<br>92° C. 45 seconds<br>55° C. 1 minute 45 seconds | 3 cycles |
| Program 3 | 70° C. 3 minutes<br>92° C. 45 seconds<br>54° C. 45 seconds | 40 cycles |
| Program 4 | 70° C. 10 minutes<br>27° C. soak | 1 cycle | c) Analysis. PCR products were analyzed using 3.5% NuSieve CTG Agarose. The results were recorded using the Eagle Eye™ still video system (Stratagene, La Jolla, Calif.).

II. RESULTS

A. Background Experiments

A series of experiments were conducted with the consensus primers 964 and 965 to test the feasibility of using Intergenic Length Polymorphism-based PCR (ILP-PCR) for detection of mycoplasma infection in cell lines.

1. Preliminary experiments consisted of determining whether consensus primers yielded a PCR fingerprint which would allow one to discriminate between infected cells and non-infected cells. Genomic DNA (gDNA) was isolated from the ALEX, L, SP20, and J558 cell lines, and subjected to a ILP-PCR analysis. Both of the infected cells gave PCR bands which could be used to clearly differentiate the infected cells from the non-infected cells. However, the non-infected cells did yield some background.

The ILP-PCR analysis of the two infected cells, ALEX and L cell, indicated that the fingerprint was different for each cell. The ALEX cell fingerprint consisted of three bands, a major band of approximately 150 bp, and two minor bands of approximately 70 bp and 250 bp. The L cell fingerprint consisted of three equally intense bands of approximately 70 bp, 150 bp, and 235 bp.

A summary of the results obtained at both facilities as to the state of Mycoplasm infection in the indicated cell lines is as follows:

| Cell | U.C.S.D. results | ILP-PCR results |
|---|---|---|
| ALEX | + | + |
| L cell | + | + |
| SP20 | − | − |
| J558 | − | − |

2. The PCR bands associated with ALEX and L cell were isolated and sequenced in an attempt to obtain data which could be used to design specific primers for mycoplasma. Based on our knowledge of tRNA genomic gene and that the 235–250 bp products should contain the coding region for two tRNA genes. Using cycle sequencing, we obtained sequence data for the 150 bp band from ALEX and 235 bp product from L cells. While the DNA sequences we obtained were not full length, they consisted of regions encoding both t-RNA gene(s) and non-coding intergenic portions.

3. Published tRNA sequence information from *M. capricolum* and *M. mycoides*, e.g., Muto et al., *Nucl. Acids Res.*, 17:5037 (1990), Samuelson, et al., *Biochem. J.*, 232:223–228 (1985), were used to 1) ask questions about the site at which the consensus primers were annealing within the tRNA complex, and 2) to design primers which would be specific for mycoplasma.

Alignment of the consensus primers, 964 and 965, with the published Mycoplasma sequence data showed that these primers were excellent consensus primers, that is, they were similar in sequence with numerous tRNAs. Sequence differences between the different tRNA genes permitted the ranking of each tRNA as to its propensity to serve a priming site for PCR. This ranking was based on the number of continuous matches between primer and tRNA bases as one moved in a 3' to 5' direction. Ranking was conducted for both primers. In theory, one should be able to take these rank orderings and to establish all the possible PCR products that might be obtained when using the particular pair of primers.

When such a combinational analysis was conducted for the primers 964 and 965, several points emerged. First, based on primer location within the tRNA genes, the PCR products should be multiples of approximately 75–86 bp. This was a reflection of tRNA gene size and typical intergenic space. Second, even within a nine member cluster such as found in the mycoplasma genome, the actual number of possible PCR products was limited. Third, to obtain multiple member fingerprints in the PCR, the most likely sites at which annealing and extension were occurring were contained within the largest member tRNA clusters. The smaller member clusters (e.g., clusters T4–T14) were not of sufficient length to yield the larger PCR products observed in initial ILP-PCR (not all the PCR products are necessarily from within the same tRNA complex). Comparing the results of this combinatorial analysis described above with the size of the actual PCR products obtained in the analysis of the ALEX cells and the L cells, suggest the site at which the consensus primers were annealing.

Based on the preliminary data, specific primers for these tRNAs were designed. We designed a 5' primer (415) which was specific for fMET$^{CAT}$ tRNA contained with the complex, and a 3' primer (416) which was specific for PHE$^{GAA}$ tRNA also contained within the complex. According to combinatorial analysis performed herein, it was highly probable that this primer pair should produce a PCR product, and the product should be approximately 150 bp in size. To increase the stringency of these primers we compared the sequence of the mycoplasma tRNA genes with the equivalent tRNA genes present in *Bacillus subtilis*, see Wawrousek, et al., *J. Biol. Chem.*, 259:3644–3702 (1984). This analysis indicated that by changing the register of the primers, particularly 416, relative to the tRNA gene one could obtain primers which would amplify mycoplasma DNA but which would fail to amplify *B. subtillus* DNA. Primer 415 was therefore offset 3 bp relative to 964, and primer 416 was offset 7 bp relative to 965.

The results of the ILP-PCR test conducted with the 415 and 416 primers were not as anticipated. When the standard ILP-PCR was conducted with gDNA from the four indicator cell lines, there was no correlation between the fingerprints which were obtained, and the state of infection. "Mix and Match" experiments between the 415–416 primer pair and the 964–965 indicated that the 3' primer (416) was faulty. That is, the 416 would not yield mycoplasma diagnostic fingerprints when used in combination with either 415 or 964, whereas the 415 primer was diagnostic when combined with the consensus primer 965. These results, indicate that the tRNA genes in cell culture mycoplasmas are quite distinct from the tRNA genes in mycoplasma strains for which the published tRNA sequences are available.

The manner in which the unique 3' end of primer 416 affects ILP-PCR was evaluated by designing a new PHE$^{GAA}$ tRNA primer (773) which, unlike the specific primer 416, was in register with the 965 consensus primer. In contrast to the 416 primer, this new primer was capable of replacing the 3' consensus primer 965 in ILP-PCR and yielding diagnostic PCR products. Interestingly, the fingerprints which were obtained were the same when either of the 3' primers, 965 or 773, was paired with either of the 5' primers. This suggests that 965 and 773 are priming from the same site within the DNA.

B. Design of PCR Primers For Detection of Mycoplasma Through ILP-PCR

Published sequence data for mycoplasma tRNA clusters was used to design primers for use in ILP-PCR. Preliminary experiments (as described above), suggested that the published mycoplasma sequences were quite different from those associated with cell culture mycoplasma. To accommodate these differences, primers were designed so as to have alignments (the "registers") same or near that of the consensus primers 964 and 965. Another primer design parameter was to consider what are the most common motifs which occur within the 964 and 965 "registers" of the T1 tRNA gene complex of *M. capricolum* or *M. mycoides* so as to maximize the possible number of PCR products. The most common motifs in the priming site from the 5' end of the T1 cluster, as well as the most common motifs in the priming site from the '3 end of the T1 cluster was also considered when designing the primers. Designing primers that incorporate these prevalent motifs from either end of the T1 tRNA cluster was expected to maximize the chance for multiple PCR products using ILP-PCR.

One primer designed using these parameters was 772, a 5' primer which was specific for the PRO$^{TGG}$ tRNA gene in *M. capricolum.* The 3' primer that met this criteria was primer 773, the previously described primer for the PHE$^{GAA}$ tRNA gene. An actual ILP-PCR analysis of the 772 primer used in combination with either the consensus primer 965, or the tRNA PHE$^{GAA}$ specific primer 773, showed the 772 primer to be effective in delineating mycoplasma infection in our four test cells. Moreover, the combination of 772 and 773 yielded the desired mix of small-to-midrange (150–700 bp) PCR products.

The primers listed in the following table had all worked in initial ILP-PCR screening of gDNA from infected and non-infected cells.

| Primer | 5' specificity | 3' specificity |
|---|---|---|
| 964 | consensus | |
| 965 | | consensus |
| 415 | f-MET | |
| 772 | PRO | |
| 773 | | PHE |
| 774 | | PHE |

C. Testing of Mycoplasma gDNA

The PCR primers were tested for their ability to amplify polynucleotides from mycoplasma and achloeplasma strains commonly associated with infection of tissue culture cells. Untitered stocks of the following mycoplasma/Achloeplasma from the American Type Culture Collection (ATCC): *Mycoplasma arginini* (cat # 23838), *Mycoplasma fermentans* (cat # 19989), *Mycoplasma hyorhinis* (cat # 23839), *Mycoplasma orale* (cat # 29802), and *Achloeplasma laidlawii* (cat # 29804). These stocks were hydrated in UV-irradiated water and used as templates for ILP-PCR.

After an initial screen of the ATCC stock for the proper dilution to use in the ILP-PCR, an exhaustive analysis of all possible primer pairs for the ability to amplify DNA from all five of the ATCC samples was conducted. The results yield several interesting insights. First, results could be grouped according to which primer was used as the 5' primer. That is, the patterns of PCR products are dictated by the 5' primer. Second, between each of the 5' groups there are primers which appear to be better at detecting all strains of mycoplasma. For instance, the 415 primer does not allow one to detect *M. fermentans* or *M. arginini.* In contrast, the 772 primer allows one to detect all, or most, strains depending on the 3' primer used. Third, within each of the groups dictated by the 5' primer, there are 3' primers that are better at detecting all forms of mycoplasma. For instance, the 772, 965 combination does not amplify the *M. fermentans*, while the 772,773 combination does. Based on these results it was decided that the 772, 773 as the primer pair would be evaluated further. The 964,965 consensus primer pair was a secondary choice, but this pair did not appear to be very efficient at amplifying off of the fermentans genome.

D. Infection of Cell Lines

The ILP-PCR fingerprint obtained with gDNA isolated from mycoplasma-infected cells was compared with the ILP-PCR fingerprint obtained with gDNA from free mycoplasma. Cells which had been infected with known strain of mycoplasmas were tested. Fresh hydrates of the five ATCC stocks were used to intentionally infect 3T6 cells. These cells were selected as targets for infection because they are sensitive to infection to mycoplasma. Two weeks after the cells were infected, gDNA was isolated from the cells using standard phenol-chloroform methods (see Methods) and tested by ILP-PCR. Both the 772,773 and 964,965 primer pairs were used in these experiments. Surprisingly, both primer pairs indicated that the cells exposed to *M. fermentans* and *M. hyorhinis* were obviously infected, whereas the cells which had been exposed to the other strains of mycoplasma were apparently not infected. These results were confirmed in parallel experiments using the MycoTect™ kit.

The following table illustrates the correlation we determined between our ILP-PCR results and the MycoTect™ kit on the testing of the 3T6 cells intentionally infected with mycoplasma.

| 3T6 infected with | ILP-PRC results | Mycotek ™ results |
|---|---|---|
| *M. arginini* | non-infected | non-infected |
| *M. fermentans* | infected | infected |
| *M. hyorhinis* | infected | infected |
| *M. orale* | non-infected | non-infected |

The infection with *Acholeplasm laidlawii* resulted in the death of 3T6 cells. No long term lines were obtained from this infection of the 3T6 cells. This result was obtained on two separate trials, each using different levels of Acholeoplasm to infect the cells.

E. Optimizing the PCR Conditions

The PCR conditions described in Welsh and McClelland, *Nucleic Acids Research*, 19:861–866 (1991), were found to be inadequate for use with the mycoplasma-specific tRNA primers described herein. This problem was corrected by including an early 3 cycle program in which the annealing temperature was lowered and the ramp rate from annealing temperature to extension temperature was decreased. Subsequent experiments in which the conditions of this short program were varied showed that it was the changes in the ramp rate, not alterations in the annealing temperature, which had made the revised PCR program function. Successful annealing could take place at a higher temperature than that used by Welsh and McClelland (55° C. versus 50° C.) if the ramp rate was low. The PCR program (see below) was redesigned with a 1) slightly longer annealing time in the program 2 (1 minute, 45 seconds versus 45 seconds), 2) a higher annealing temperature in programs 1, 2 and 3 (55° C. versus 50° C.), and 3) an elimination of the long annealing time commonly used by many researchers prior to initiating the main program (1 minute 45 seconds versus 5 minutes). The changes from the program of Welsh and McClelland are highlighted in the modified PCR shown here.

| Program 1 | 92° C. 5 minutes | 1 cycles |
| | 55° C. 1 minute 45 seconds | |
| Program 2 | 70° C. 3 minutes | 3 cycles |
| | 92° C. 45 seconds | |
| | 55° C. 1 minute 45 seconds | |
| Program 3 | 70° C. 3 minutes | 40 cycles |
| | 92° C. 45 seconds | |
| | 55° C. 45 seconds | |
| Program 4 | 70° C. 10 minutes | 1 cycle |
| | 27° C. soak | |

Using this program with gDNA (genomic DNA) obtained from 3T6 infected with *M. fermentans* or *M. hyorhinis* gave excellent results. The bands were clear, and of the size expected from previous experiments. In contrast gDNA from non-infected cells gave a clear lane when the PCR sample was analyzed on agarose gels. Parallel retesting of the mycoplasm/acholeplasm obtained from ATCC gave fingerprints which were identical to the earlier experiments. Therefore, these conditions were established as the standard to be used in subsequent testing.

These results suggest that the early 3 cycle program is necessary to allow for annealing of primers to substrates which are present in low number, and for which there is not an exact match between primer and template. Later annealing events proceed faster because an exact match has been established between primer and template.

F. Testing of Trial Cells Line with Optimal Primers and Optimal PCR Conditions The object of these experiments were two-fold: to verify the optimization of the signal-to-noise ratio, and to verify that the results correlated with results obtained by other testing methods.

In the first experiments, we analyzed gDNA from ALEX, L cell SP20, J558, those cells lines whose mycoplasma status we already knew. The results indicate that the modified PCR method and the 772/773 primers yielded information which was unambiguous. Contaminated cell lines gave distinctive fingerprints, while non-contaminated cells yielded no perceivable products, even when analyzed using the Eagle-Eye™ (from Stratagene) video system.

G. Method for Template Preparation

Experiments conducted to this point had utilized gDNA prepared by standard means i.e., phenol/chloroform extraction and ethanol precipitation. Alternative methods of template preparation were tried.

Preparation of the templates by boiling the cells to be analyzed was found to be compatible with the subject ILP-PCR test. To conduct this extraction, cells were washed with phosphate-buffered saline (PBS). This washing step removed components in media which interfere with ILP-PCR. Known numbers of cells were then aliquoted into eppendorf tubes, pelleted through centrifugation, and the cell pellet was resuspended in 100 µl of 1X Taq polymerase buffer. The cell solution was then boiled for 15 minutes, and re-centrifuged to remove particulate matter. We determined that we could extend the upper range of cell equivalents over which the PCR test was effective by adding Straclean (10 µl) to the cell extract after the initial centrifugation.

H. Sensitivity of the PCR-Based Assay

The sensitivity of the ILP-PCR assay towards mycoplasma was analyzed. These experiments were conducted by infecting 3T6 cells with *Mycoplasma hyorhinis* or *fermentans*. The cells were harvested, washed, and counted. One million cells were placed into an eppendorf tube and extracted with 100 μl of 1X Taq buffer as described above. Ten-fold dilutions of the extract were the used as templates in the ILP-PCR assay. Results with cells infected with *Mycoplasma hyorhinis* demonstrate the range over which the ILP-PCR is suitable for detection of mycoplasma. At the upper end of the experiment, the assay detected mycoplasma infection at $10^5$ cell equivalents. At the lower end of the scale, the assay detected mycoplasma infections at 10 cells equivalents. At one cell equivalent the signal became weak, and disappeared at one-tenth of a cell equivalent. Preliminary experiments demonstrated inhibition at higher cell input due to carryover of components found in the media. By increasing the thoroughness of the PBS wash (three washes instead of one) conducted prior to extracting the cells, we eliminated the inhibition. In parallel, it was found that treatment of the extracts with Stratclean™ (available from Stratagene) removed inhibitory compounds which interfered with the test at higher cell inputs.

I. Specificity of the PCR-Based Assay

ILP-PCR makes use of the conservation of the tRNA sequences within a species to generate diagnostic fingerprints. The results obtained with free mycoplasma indicate that the 772/773 primer combination generated unique fingerprints for each species. However, the general conservation of tRNA gene sequences over a wide range of species might pose a potential problem for using ILP-PCR in the identification of mycoplasma, namely, the question of specificity. To determine the specificity of ILP-PCR for mycoplasma, experiments were performed to determine what other microbes the 772/773 primer combination might detect, and how these fingerprints would compare to those we had obtained with Mycoplasma/Acholeoplasma templates. Before initiating these experiments, a homology search was performed comparing the 772 and 773 sequence to all known sequences contained within GenBank. The comparison used the 1992 version of the GenBank database, search was conducted using the MacVector™ program. The results of this search indicated that the 772/773 primers were similar in sequence to portions of the tRNA genes present in other microorganisms, particularly, Bacillus and Escherichia. To determine if this homology would be a problem, sources of polynucleotides from *Bacillus globilii, Escherichia coli,* and Staphylcoccus were obtained and run in the standard ILP-PCR using the 772/773 primer combination. The results demonstrate that a fingerprint is obtained when DNA from each of these organisms is tested in the ILP-PCR. However, these fingerprints are clearly different from those obtained with Mycoplasma/Acholeplasma. Even if fingerprints are obtained which are due to non-mycoplasma contaminants, the investigator will know that he/she has a major problem with the cell line which is being tested.

J. Reproducibility of the PCR-Based Test on Other Thermocyclers

ILP-PCR using the 772/773 primers was performed under standard optimal reaction conditions using a variety of PCR thermocyclers in order to demonstrate that the results obtained were not specific to any machine. To conduct these experiments, a common reaction mixture was created was created, including primers and templates, and aliquoted into PCR tubes that were compatible with the machines to be tested. This procedure ensured that the reaction mixtures would be common to all samples. Templates included polynucleotides from bona-fide infected 3T6 cell lines, gDNA from non-infected 3T6 cell lines, gDNA from non-infected Sp20 cell lines, and gDNA from 3T6 cells that were subjected to attempts to be infected with *Mycoplasma orale* and were shown to be non-infected in previous experiments. Three different machines were tested: the Techne machine which had used to conduct the previous experiments, a Cetus 9600, and a Cetus thermocyler. Identical PCR programs, and cycle number were used with each machine. These samples were all analyzed together. The results indicated that all machines gave equivalent fingerprint patterns. There was some variation in band intensity, the Cetus 9600 giving the lowest band intensity, and the Techne and the Cetus thermocycler giving similar band intensity.

EQUIVALENTS

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The foregoing written specification is considered to be sufficient to enable one skilled in the art to practice the invention. Indeed, various modifications of the above-described modes for carrying out the invention which are obvious to those skilled in the field of molecular biology or related fields are intended to be within the scope of the following claims.

---

What is claimed is:

1. A method of detecting mycoplasma in a sample for analysis, said method comprising the steps,
   isolating polynucleotides from said sample for analysis, whereby a polynucleotide sample is produced
   adding a pair of polynucleotide primers which hybridize to a mycoplasma tRNA gene, to said polynucleotide sample,
   amplifying at least a portion of at least one tRNA gene cluster by a cyclic amplification reaction employing said primers, whereby at least one amplification product is produced, and detecting said amplified product, wherein said detection of amplified probe is indicative of the presence of mycoplasma,
   wherein said pair of primers is selected from the group consisting of:

(a) Primer 772 5'CGAAGGGTCGCAGGTTCAAA3'
       (SEQ ID No: 1), and
       Primer 773 5'CTCAGTCGGTAGAGCAGCAGA3'
       (SEQ ID No: 2),
   (b) Primer 772 5'CGAAGGGTCGCAGGTTCAAA3'
       (SEQ ID No: 1), and
       Primer 965 5'AGTCCGGTGCTCTAACCAACTGAG3'
       (SEQ ID No: 5),
   (c) Primer 964 5'AGGTCGCGGGTTCGAATCC3'
       (SEQ ID No: 4), and
       Primer 773 5'CTCAGTCGGTAGAGCAGCAGA3'
       (SEQ ID No: 2),
   (d) Primer 964 5'AGGTCGCGGGTTCGAATCC3'
       (SEQ ID No: 4), and
       Primer 774, 5'CTCAGTCGGTTAGAGCAGCAG3'
       (SEQ ID No: 3),
   (e) Primer 415 5'CGGAGGYCGCAGGTTCGAG3'
       (SEQ ID No: 6), and
       Primer 965 5'AGTCCGGTGCTCTAACCAACTGAG3'
       (SEQ ID No: 5),
   (f) Primer 415 5'CGGAGGYCGCAGGTTCGAG3'
       (SEQ ID No: 6), and
       Primer 773 5'CTCAGTCGGTAGAGCAGCAGA3'
       (SEQ ID No: 2),
   (g) Primer 415 5'CGGAGGYCGCAGGTTCGAG3'
       (SEQ ID No: 6), and
       Primer 774 5'CTCAGTCGGTTAGAGCAGCAG3'
       (SEQ ID No: 3), and
   (h) Primer 773 5'CTCAGTCGGTAGAGCAGCAGA3'
       (SEQ ID No: 2), and
       Primer 772 5'CGAAGGGTCGCAGGTTCAAA3'

-continued (SEQ ID No: 1).

2. A method according to claim 1, wherein said method further comprises the step of separating said amplification product by electrophoresis.

3. A method according to claim 1, wherein said polynucleotide primers are capable of hybridizing to a plurality of tRNA gene clusters.

4. A method according to claim 1, said method further comprising the step of adding internal amplification control sequence, wherein said internal amplification control sequence is capable of hybridizing to both of said primers.

5. A polynucleotide primer wherein the primer consists of the nucleotide sequence selected from the group consisting of:

Primer 772 5'CGAAGGGTCGCAGGTTCAAA3'
(SEQ ID No: 1),
Primer 773 5'CTCAGTCGGTAGAGCAGCAGA3'
(SEQ ID No: 2),
Primer 774, 5'CTCAGTCGGTTAGAGCAGCAG3'
(SEQ ID No: 3),
and Primer 415 5'CGGAGGYCGCAGGTTCGAG3'
(SEQ ID No: 6).

6. A pair of polynucleotide primers, wherein said primers is selected from the group consisting of:

(a) Primer 772 5'CGAAGGGTCGCAGGTTCAAA3'
       (SEQ ID No: 1), and
       Primer 773 5'CTCAGTCGGTAGAGCAGCAGA3'
       (SEQ ID No: 2),
   (b) Primer 772 5'CGAAGGGTCGCAGGTTCAAA3'
       (SEQ ID No: 1), and
       Primer 965 5'AGTCCGGTGCTCTAACCAACTGAG3'
       (SEQ ID No: 5),
   (c) Primer 964 5'AGGTCGCGGGTTCGAATCC3'
       (SEQ ID No: 4), and
       Primer 773 5'CTCAGTCGGTAGAGCAGCAGA3'
       (SEQ ID No: 2),
   (d) Primer 964 5'AGGTCGCGGGTTCGAATCC3'
       (SEQ ID No: 4), and
       Primer 774, 5'CTCAGTCGGTTAGAGCAGCAG3'
       (SEQ ID No: 3), (e) Primer 415 5'CGGAGGYCGCAGGTTCGAG3'
(SEQ ID No: 6), and
Primer 965 5'AGTCCGGTGCTCTAACCAACTGAG3'
(SEQ ID No: 5),
(f) Primer 415 5'CGGAGGYCGCAGGTTCGAG3'
(SEQ ID No: 6), and
Primer 773 5'CTCAGTCGGTAGAGCAGCAGA3'
(SEQ ID No: 2),
(g) Primer 415 5'CGGAGGYCGCAGGTTCGAG3'
(SEQ ID No: 6), and
Primer 774 5'CTCAGTCGGTTAGAGCAGCAG3'
(SEQ ID No: 3), and
(h) Primer 773 5'CTCAGTCGGTAGAGCAGCAGA3'
(SEQ ID No: 2), and
Primer 772 5'CGAAGGGTCGCAGGTTCAAA3'
(SEQ ID No: 1).

7. A kit for detecting the presence of a mycoplasma in a sample for analysis, said kit comprising, a pair of polynucleotides according to claim 6.

8. A kit according to claim 7, said kit further comprising an internal amplification control sequence.

\* \* \* \* \*

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:1:

CGAAGGGTCG CAGGTTCAAA　　　　　　　　　　　　　　　　　　　　　　　　　　　　　　20

( 2 ) INFORMATION FOR SEQ ID NO:2:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:2:

CAGTCTGCTG CTCTACCGAC TGAG　　　　　　　　　　　　　　　　　　　　　　　　　　24

( 2 ) INFORMATION FOR SEQ ID NO:3:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:3:

CTCAGTCGGT TAGAGCAGCA G　　　　　　　　　　　　　　　　　　　　　　　　　　　21

( 2 ) INFORMATION FOR SEQ ID NO:4:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:4:

AGGTCGCGGG TTCGAATCC　　　　　　　　　　　　　　　　　　　　　　　　　　　　19

( 2 ) INFORMATION FOR SEQ ID NO:5:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:5:

AGTCCGGTGC TCTAACCAAC TGAG 24

( 2 ) INFORMATION FOR SEQ ID NO:6:

( i ) SEQUENCE CHARACTERISTICS:
( A ) LENGTH: 19 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:6:

CGGAGGYCGC AGGTTCGAG 19